(12) United States Patent
Kusleika et al.

(10) Patent No.: US 6,843,798 B2
(45) Date of Patent: Jan. 18, 2005

(54) SLIDEABLE VASCULAR FILTER

(75) Inventors: Richard S. Kusleika, Eden Prairie, MN (US); Brian V. Finander, Vadnais Heights, MN (US)

(73) Assignee: ev3 Inc., Plymouth, MN (US)

( * ) Notice: Subject to any disclaimer, the term of this patent is extended or adjusted under 35 U.S.C. 154(b) by 346 days.

(21) Appl. No.: 10/084,263

(22) Filed: Feb. 27, 2002

(65) Prior Publication Data

US 2002/0123720 A1 Sep. 5, 2002

Related U.S. Application Data

(63) Continuation of application No. PCT/US99/19942, filed on Aug. 27, 1999.

(51) Int. Cl.[7] .............................................. A61M 29/00
(52) U.S. Cl. ...................................................... 606/200
(58) Field of Search ................................ 606/113, 114, 606/127, 200, 159

(56) References Cited

U.S. PATENT DOCUMENTS

| | | | |
|---|---|---|---|
| 5,814,064 A | | 9/1998 | Daniel |
| 6,179,859 B1 | * | 1/2001 | Bates et al. .................. 606/200 |
| 6,325,815 B1 | | 12/2001 | Kusleika |
| 6,336,934 B1 | * | 1/2002 | Gilson et al. ................ 606/200 |
| 6,371,971 B1 | | 4/2002 | Tsugita et al. |
| 2001/0012951 A1 | | 8/2001 | Bates et al. |
| 2001/0041908 A1 | | 11/2001 | Levinson et al. |

FOREIGN PATENT DOCUMENTS

| | | |
|---|---|---|
| EP | 820729 | 1/1998 |
| WO | WO 96/01591 | 1/1996 |
| WO | WO 98/39053 | 9/1998 |
| WO | WO 99/23976 | 5/1999 |
| WO | WO 01/15629 | 3/2001 |
| WO | WO 01/21100 | 3/2001 |

* cited by examiner

Primary Examiner—Kevin T. Truong
(74) Attorney, Agent, or Firm—Popovich, Wiles & O'Connell, P.A.

(57) ABSTRACT

A collapsible medical device for use, e.g., as a vascular filter. The device includes a mandrel having a distal end and a stop spaced proximally of the distal end. A proximal length of the mandrel extends proximally of the stop and a distal length of the mandrel extends distally of the stop. A functional element (e.g., a vascular filter) has a radially expandable body and includes a proximal slider and a distal slider. The proximal and distal sliders are slidable along the mandrel independently of one another such that the distance between the proximal slider and distal slider can be varied to effect different configurations of the functional element. In one method of using such a device, the functional element is urged distally to a treatment site by urging the mandrel distally. This causes the stop to exert a distal biasing force on the distal slider, which acts against a restorative force of the functional element to axially elongate the functional element and reduce friction between the functional element and a wall of the vessel.

25 Claims, 11 Drawing Sheets

SLIDEABLE VASCULAR FILTER

This is a continuation of International Application No. PCT/US99/19942, filed Aug. 27, 1999, the contents of which are hereby incorporated by reference into this application.

FIELD OF THE INVENTION

The present invention provides a medical device which can employed in a minimally invasive medical procedure, e.g., by deploying it in a blood vessel through a catheter. While a variety of such medical devices can be made in accordance with the invention, the invention is particularly useful as a filter for use in a blood vessel or other channel in a patient's body.

BACKGROUND OF THE INVENTION

Filters can be deployed in channels or vessels in patient's bodies in a variety of medical procedures or in treating certain conditions. For example, rotating burrs are used in removing atheroma from the lumen of patients' blood vessels. These burrs can effectively dislodge the atheroma, but the dislodged material will simply float downstream with the flow of blood through the vessel. Filters can be used to capture such dislodged material before it is allowed to drift too far downstream, possibly occluding blood flow through a more narrow vessel.

Some researchers have proposed various traps or filters for capturing the particulate matter released or created in such procedures. However, most such filters generally have not proven to be exceptionally effective in actual use. These filters tend to be cumbersome to use and accurate deployment is problematic because if they are not properly seated in the vessel they can drift to a more distal site where they are likely to do more harm than good. In addition, these filters are generally capable of only trapping relatively large thrombi and are not effective for removing smaller embolic particles from the blood stream.

The problems with most temporary filters, which are intended to be used only during a particular procedure then retracted with the thrombi trapped therein, are more pronounced. Even If the trap does effectively capture the dislodged material, it has proven to be relatively difficult or complex to retract the trap back into the catheter through which it was delivered without simply dumping the trapped thrombi back into the blood stream, defeating the purpose of the temporary filter device. For this reason, most atherectomy devices and the like tend to aspirate the patient's blood during the procedure to remove the dislodged material entrained therein.

One promising filter design which overcomes many of these difficulties is shown in International Publication No. WO 96/01591 (the publication of PCT International Application No. PCT/US95/08613), the teachings of which are incorporated herein by reference. Generally, this reference teaches a trap which can be used to filter particles from blood or other fluid moving through a body vessel. In one illustrated embodiment, this trap includes a basket 270 which can be deployed and retracted through a catheter or the like, making it particularly suitable for use in minimally invasive procedures such as angioplasty or atherectomy procedures. The fact that this trap is optimally carried on a mandrel 260 further enhances its utility as most common angioplasty balloons and atherectomy devices are used in conjunction with such mandrels. While this trap is very useful and shows great promise in many common procedures, it may be possible to improve the ease with which it may be deployed and/or retracted.

Some medical devices are also permanently deployed in a patient's vessel, but properly positioning these devices at the desired treatment site using minimally invasive techniques can be cumbersome. For example, occlusion devices can be used to occlude an arterial vessel or a septal defect. Some of these occlusion devices may radially expand into an enlarged configuration wherein they substantially fill the lumen of the vessel or extend over the margins on either side of a septal defect. When deploying these occlusion devices through a delivery catheter, though, the friction between the occlusion device and the wall of the catheter can make it difficult to deploy the device at a precisely selected location. These problems are even more pronounced in longer catheters tracking through more tortuous paths.

SUMMARY OF THE INVENTION

The present invention provides a medical device which can easily be deployed and retracted during a minimally invasive medical procedure. In one preferred embodiment, the medical device may take the form of a filter useful in any channel of a patient's body, be it in a blood vessel, urinary tract, or other type of vessel.

One embodiment of the invention provides a collapsible medical device including a mandrel and a functional element of any desired shape to achieve a particular end. The mandrel has a distal end and a stop spaced proximally of the distal end. A proximal length of the mandrel extends proximally of the stop and a distal length of the mandrel extends distally of the stop. The functional element includes a radially expandable body having a proximal slider and a distal slider. The proximal slider is slidably carried along the proximal length of the mandrel and the distal slider is slidably carried along the distal length of the mandrel. The proximal and distal sliders are slidable along the mandrel independently of one another such that the distance between the proximal slider and the distal slider can be varied to effect different configurations of the functional element.

A medical device in accordance with another embodiment of the invention includes a mandrel and a suitably shaped functional element. Like the prior embodiment, this mandrel has a distal end and a stop spaced proximally of the distal end. A proximal length of the mandrel extends proximally of the stop and a distal length of the mandrel extends distally of the stop. The functional element of this embodiment has a radially expandable body having a radially expanded configuration and adapted to resiliently assume the radially expanded configuration in the absence of a countervailing biasing force. The radially expandable body is attached to the mandrel by a proximal slider and a distal slider. The proximal slider is slidably carried along the proximal length of the mandrel and the distal slider is slidably carried along the distal length of the mandrel. The proximal and distal sliders are slidable along the mandrel independently of one another such that the distance between the proximal and distal sliders can be varied to effect different configurations of the body.

In one particular adaptation of the invention, the medical device has a mandrel generally as described above and also includes a functional element. The functional element of this embodiment is formed of a resilient tubular braid which has a preferred radially expanded configuration but will assume a radially reduced profile upon axial elongation. Proximal and distal sliders are attached to the tubular braid with a length of the braid extending therebetween. The proximal slider is slidably carried along the proximal length of the mandrel and the distal slider is slidably carried along the distal length of the mandrel. The proximal and distal sliders are slidable along the mandrel independently of one another.

Yet another embodiment of the invention provides a filter system which may be temporarily deployed in a channel of a patient's body. This device includes a mandrel having a distal end and an enlarged diameter stop carried proximally of the distal end. A filter is formed of a resilient tubular braid and includes proximal and distal sliders. The proximal slider is slidably carried along the mandrel proximally of the stop and the distal slider is carried along the mandrel between the stop and the distal end of the mandrel. The filter has a collapsed configuration wherein the sliders are spaced from one another a first distance along the mandrel and the filter has a first diameter. The filter also has an expanded configuration wherein the sliders are spaced a second, shorter distance along the mandrel and the filter has a second diameter. The filter's first diameter is less than its second diameter.

The present invention also contemplates a method of employing a medical device in a lumen vessel. This medical device desirably comprises a mandrel having a distal end and a stop spaced proximally of the distal end. It also includes a functional element, which may be formed of a resilient tubular braid and include proximal and distal sliders, with the proximal slider being slidably carried along the mandrel proximally of the stop and the distal slider being carried along the mandrel between the stop and the distal end of the mandrel. The distal end of the mandrel is inserted in the lumen of the vessel. The functional element is urged distally along the lumen to a treatment site by urging the mandrel distally such that the stop engages the distal slider and exerts a distal biasing force thereon. This distal biasing force acts against a restorative force of the functional element to axially elongate the functional element and reduce friction between the functional element and a wall of the vessel.

DETAILED DESCRIPTION OF THE PREFERRED EMBODIMENTS

Figure 1:
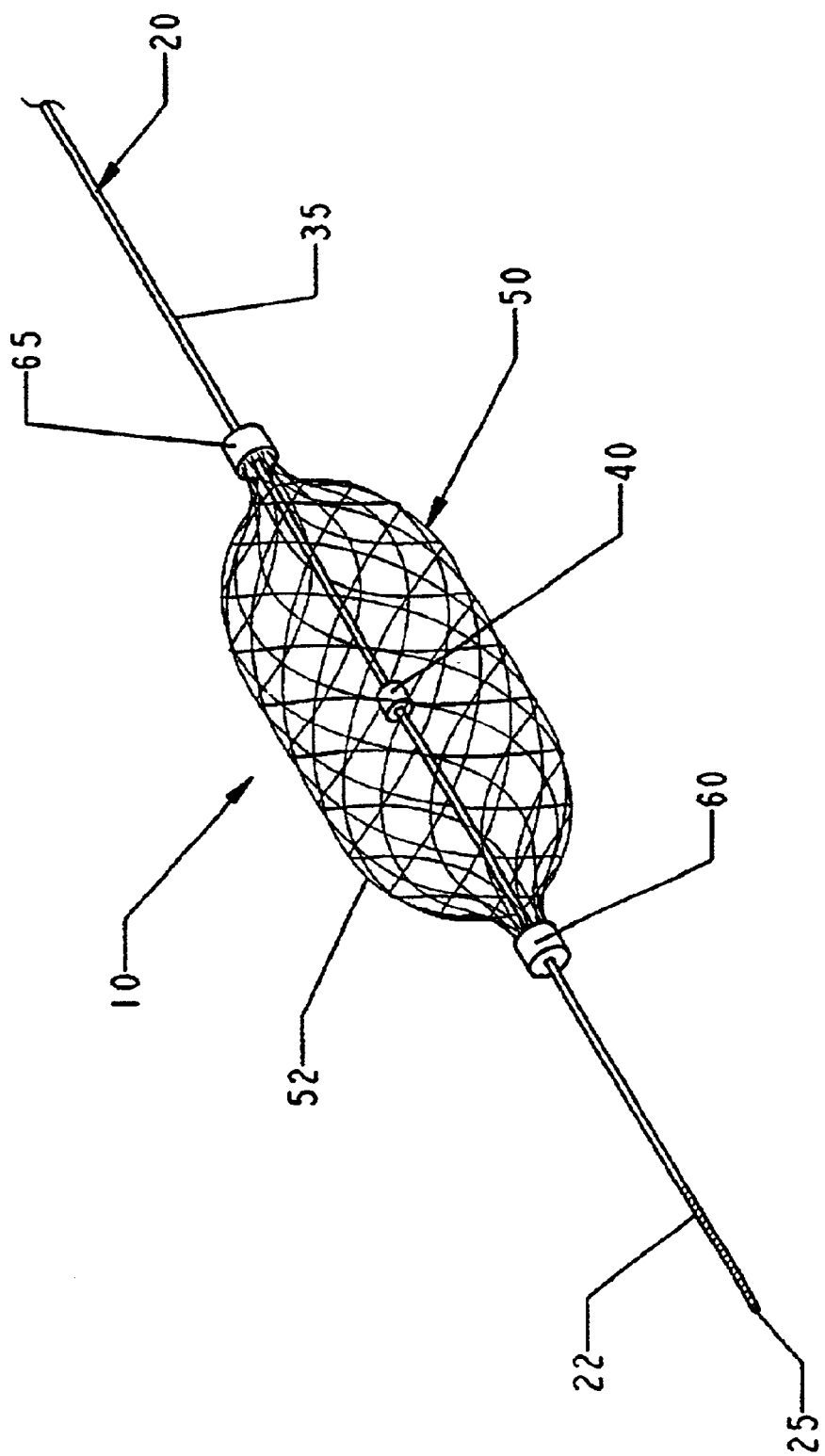
FIG. 1 is a schematic perspective view of one medical device in accordance with the invention in its deployed state.
Figure 2:
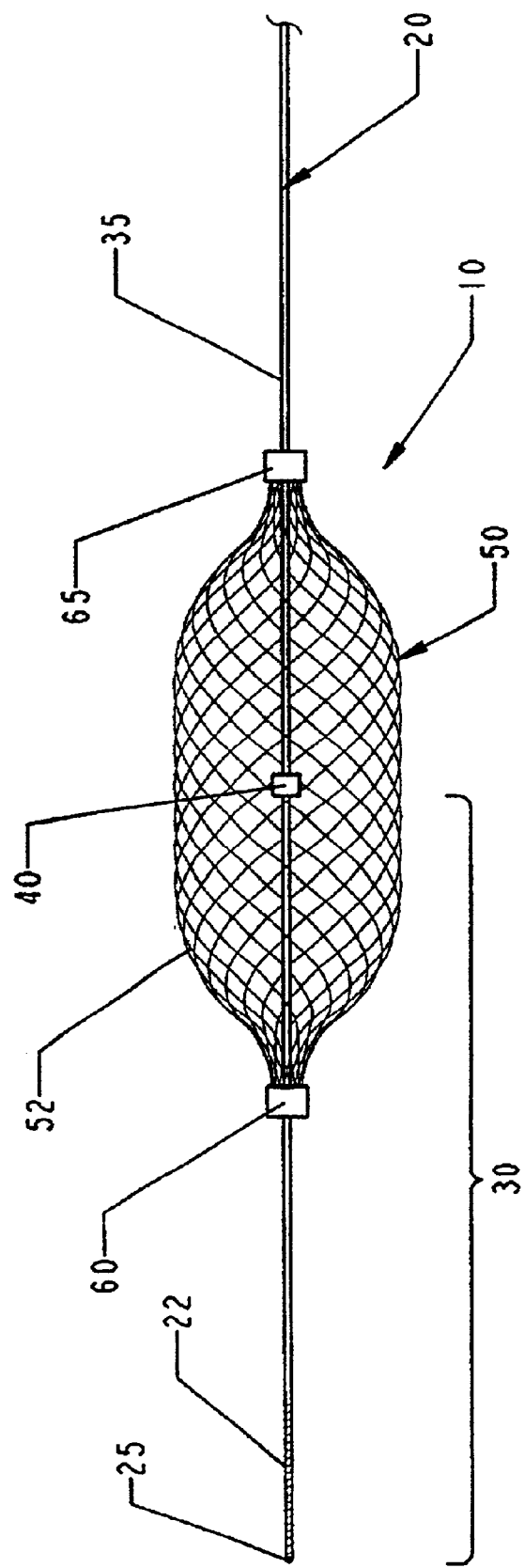
FIG. 2 is a schematic side view of the medical device of FIG. 1, also in its deployed state.

FIGS. 1 and 2 are schematic illustrations of one medical device in accordance with the present invention. This medical device comprises a filter system 10 which can be deployed in a channel in a patient's body. As noted above, this filter can be used in any channel in a patient's body, including blood vessels, the urinary tract or biliary tract and airways. This filter system 10 is optimally designed to be deployed in a patient's vessel in a minimally invasive procedure, such as by introducing the filter system into a blood vessel through an introducing catheter (not shown in FIGS. 1 and 2).

The filter system 10 of the invention generally includes a mandrel 20 and a filter 50. Conceptually, the mandrel 20 can be thought of as having a primary function of positioning and controlling the deployment of the filter 50 while the filter can be considered the primary therapeutic or functional element of the system 10.

The mandrel 20 should be fairly flexible to allow the device to be deployed in a curving body passageway without kinking or otherwise inhibiting suitable deployment of the filter 50. While the mandrel can be formed of any material having any dimension suitable for the task for which the filter system 10 is to be employed, in most circumstances, the mandrel 20 will comprise an elongate metal wire. In one particularly preferred embodiment, the mandrel 20 is formed of nitinol, a roughly stoichiometric alloy of nickel and titanium having excellent "superelastic" properties. The use of nitinol in medical guidewires and related applications is well known in the art and need not be discussed in detail here. If so desired, the distal-most length of the mandrel may include a flexible helically wound coil 22 extending thereover. The use of such helical coils to enhance flexibility of the distal tip is well known in the guidewire art.

The mandrel 20 has an enlarged diameter stop 40 attached thereto. The stop 40 is spaced proximally from the distal tip 25 of the mandrel 20. Desirably, the stop 40 is spaced proximally of the proximal end of the helical coil 22 of the mandrel. This permits the distal slider 60 of the filter 50 to slide relatively freely and unencumbered along the length of the mandrel distally of the stop.

The stop 40 can be formed of any desired material and can be attached to the mandrel 20 in any desired fashion. The stop should be attached to the mandrel relatively securely, though, as the stop will be used to urge the filter 50 within the lumen of the vessel in which the system 10 is to be deployed. As an example, the stop 40 may comprise a standard radiopaque marker band which has been securely crimped on the mandrel 20 and/or attached to the mandrel using an adhesive or solder. The precise length and shape of the stop 40 is not critical. The drawings illustrate the stop 40 as a relatively short cylindrical body attached about the circumference of the mandrel. However, the stop 40 may have a more bulbous shape and could, in theory, even be formed integrally with the mandrel.

The stop 40 effectively divides the mandrel into distal and proximal lengths. The distal length 30 of the mandrel can be thought of as that length which extends distally from the stop 40 to the distal tip 25 of the mandrel. Likewise, the proximal portion 35 of the mandrel 20 can be thought of as comprising the length of the mandrel extending proximally from the stop 40 to the proximal end of the mandrel.

The filter 50 shown in FIGS. 1–5 has an elongate, generally tubular body 52 which extends from a distal slider 60 proximally to a proximal slider 65. The body 52 of the filter can be formed of any material suitable for the application at hand. In many applications, e.g., filtering blood within a patient's vasculature the filter body 52 typically comprises a length of a braided tubular fabric. The use of a tubular braid of nitinol to make medical devices is described in some detail in International Publication No. WO 96/01591, the teachings of which were incorporated above by reference. Briefly speaking though, this process can employ a tubular braid of a fabric comprising two sets of nitinol wires wrapped helically about a mandrel, with one set of wires being wrapped spirally about the mandrel in one direction and the other set being wrapped in the other direction. This braid is then placed in contact with a molding surface of a molding element which defines the shape of the desired functional element. By heat treating the fabric in contact with the molding surface of the molding element, one can create a functional element having virtually any desired shape.

The body 52 of the filter 50 desirably is made of a fairly flexible, resilient material. In particular, the filter 52 desirably has a radially expanded configuration, e.g., the shape shown in FIGS. 1–3, which the device will tend to resiliently assume in the absence of any countervailing biasing force. A body 52 formed of a nitinol tubular braid which has been heat set into the desired shape should suit this purpose well.

Figure 7:
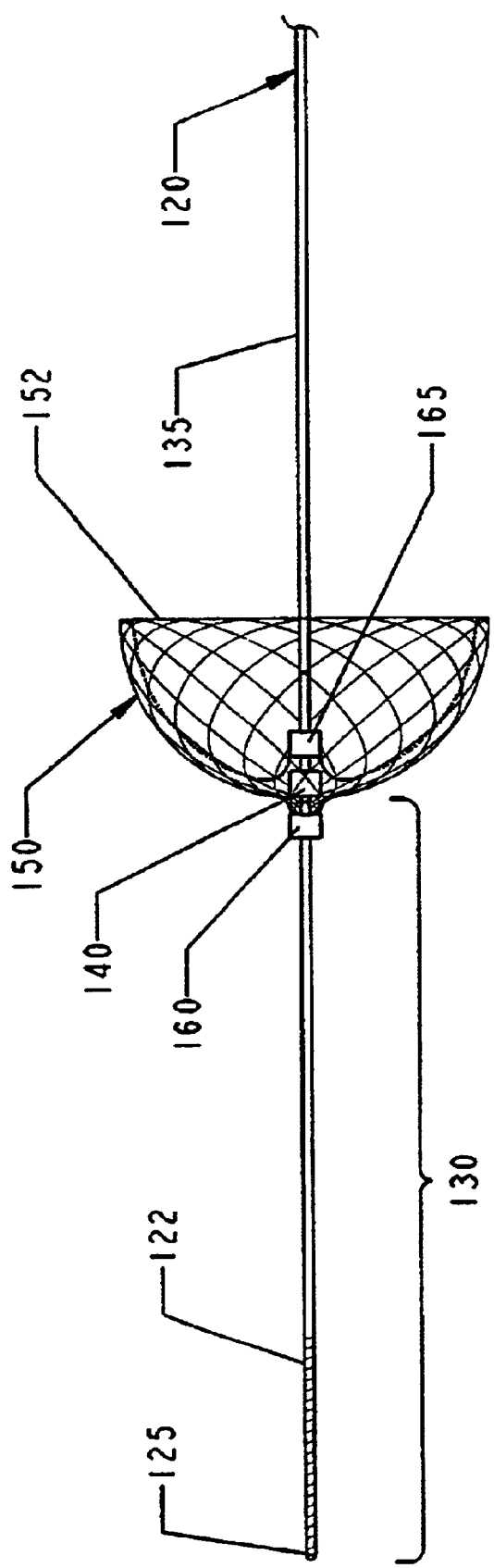
FIG. 7 is a schematic side view of an alternative medical device of the invention in its deployed state.
Figure 8:
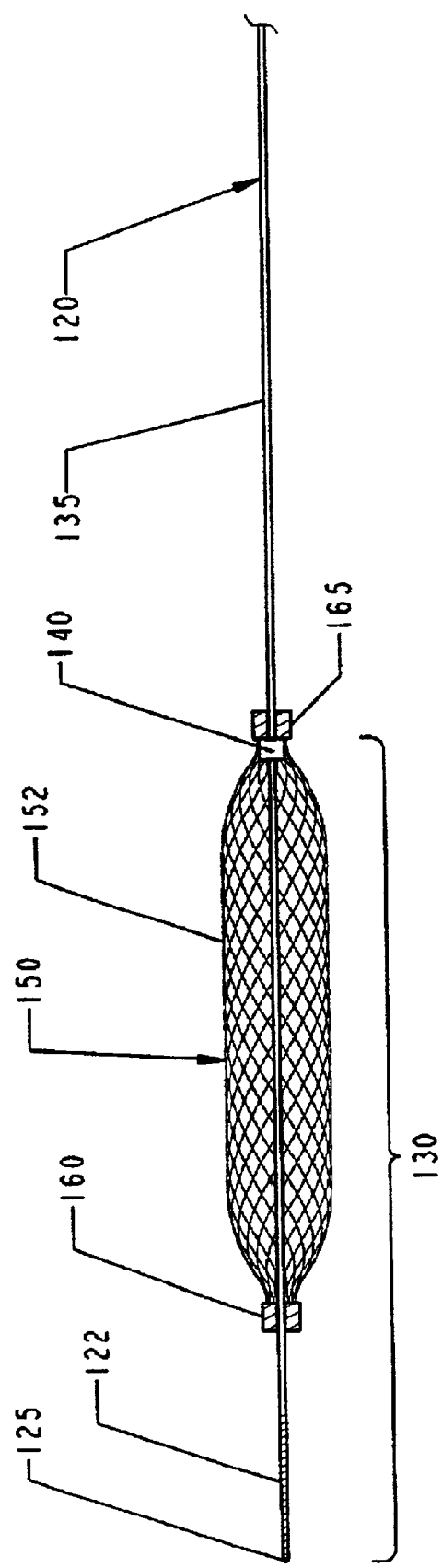
FIG. 8 is a schematic side view in partial cross section of the medical device of FIG. 7, but in a partially collapsed configuration induced by withdrawing the mandrel proximally within a vessel.
Figure 11:
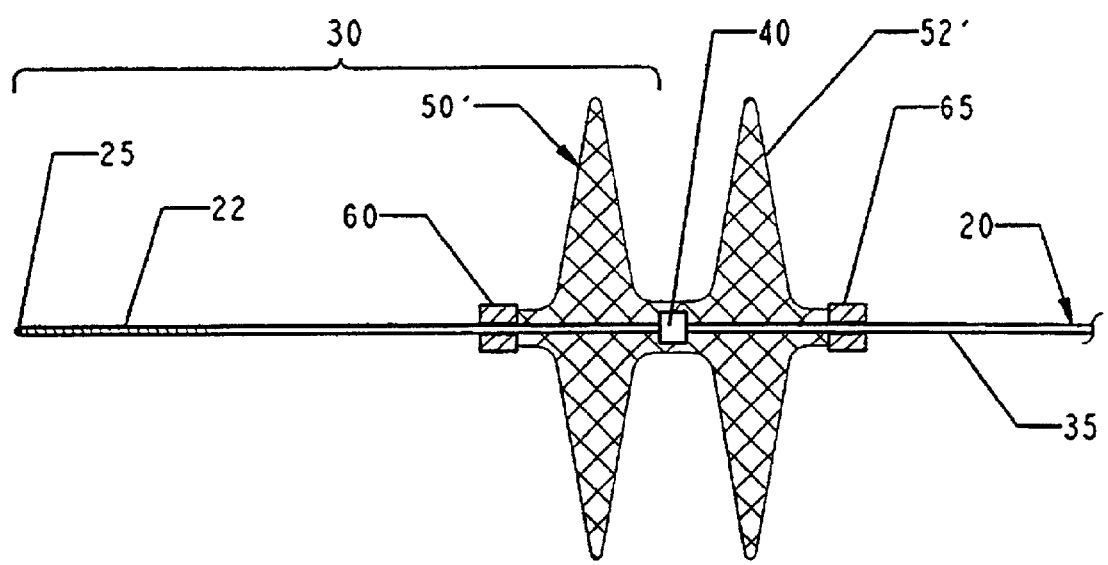
FIG. 11 is a schematic side view in partial cross section of a medical device in accordance with another embodiment of the invention in its deployed state.

In the filter system 10 shown in FIGS. 1–5, the body 52 of the filter 50 assumes a generally tubular shape having tapered proximal and distal ends. The outer diameter of the generally cylindrical middle length of the body 52 should be sized to substantially fill the lumen of a vessel to ensure that the filter will effectively trap any emboli which may be entrained in the patient's bloodstream. As will be discussed in more detail below, an alternative configuration of a filter body 152 is illustrated in FIGS. 7 and 8 and medical devices intended to achieve different clinical objectives are shown in FIGS. 11 and 13. A variety of other filter shapes, as well as shapes of other types of medical devices should be readily apparent to one of ordinary skill in the art in light of the present teachings.

The filter 50 is attached to or carried by the mandrel 20 by means of a proximal slider 65 attached to the body 52 adjacent its proximal end and a distal slider 60 attached adjacent the distal end of the body 52. The distal slider 60 should be free to slide along at least a proximal portion of the distal length 30 of the mandrel while the proximal slider 65 should be free to slide along at least a distal portion of the proximal length 35 of the mandrel. For reasons discussed more fully below in connection with FIGS. 3–5, the stop 40 of the mandrel effectively defines a limit on the range of motion of these sliders 60, 65.

While each of the sliders 60, 65 should be slidable along its respective length of the mandrel, the sliders can take any desired shape. In the illustrated embodiments, each slider comprises a relatively thin ring which is carried about the mandrel. The thin ring can be attached to the body 52 in any desired fashion, such as by crimping or swaging the fabric of the body between two layers of the ring or soldering, welding or otherwise adhering the fabric to the ring. The structure of one suitable distal slider is schematically illustrated in a more detailed cross section in FIG. 6. The proximal slider may have substantially the same configuration, but is not shown in this view simply for purposes of clarity.

Figure 6:
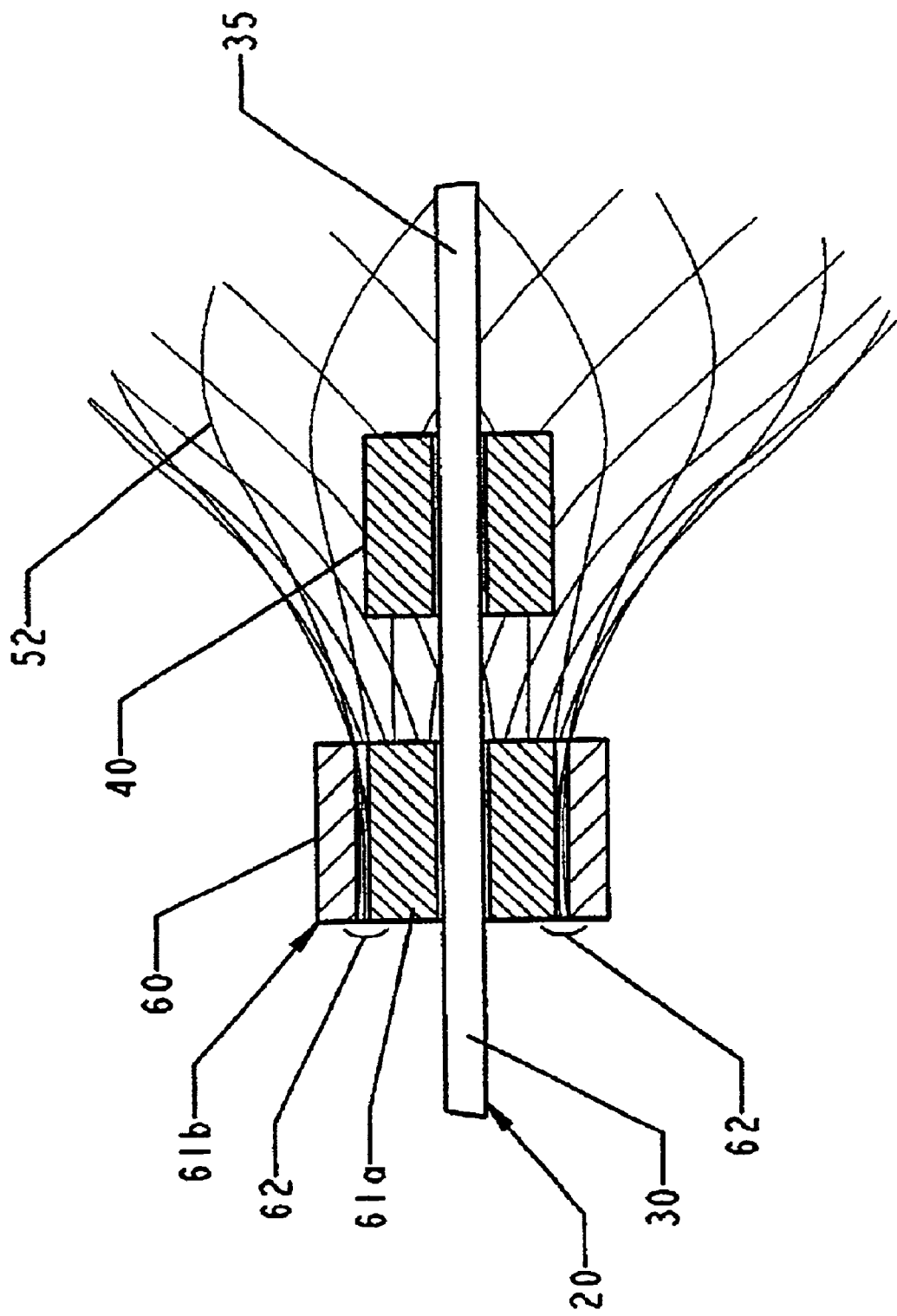
FIG. 6 is a schematic isolation view in partial cross section of the medical device of FIGS. 1 and 2, showing the relationship between the mandrel, the stop and the distal slider.

In the embodiment illustrated in FIG. 6, the distal slider 60 comprises a relatively rigid annular ring 61 having an inner component 61a and an outer component 61b. One or both components of the ring 61 is preferably formed of a radiopaque material to enable a physician to better visualize the position of the slider 60 during a procedure. The inner component 61a of the ring is received within the outer component 61b and defines an annular space therebetween. The inner diameter of the inner component is larger than the outer diameter of the mandrel 20 to facilitate sliding of the ring 61 with respect thereto. Movement of the slider 60 with respect to the mandrel can be further facilitated by coating one or both of the inner surface of the inner component 61a and the outer surface of the mandrel 20 with a friction-reducing coating, such as Teflon or a lubricious hydrophilic coating.

A distal length of the fabric of the body 52 is received in the annular space between the interior and exterior components 61a and 61b of the ring. The fabric is held in place in this space in any suitable manner, e.g. by means of a suitable solder or adhesive or by crimping the fabric between the inner and outer components. FIG. 6 schematically illustrates both approaches, with the fabric being frictionally grasped between the two components of the ring 61 and held in place by a weldment or adhesive connection 62 at the distal end of the ring.

Figure 3:
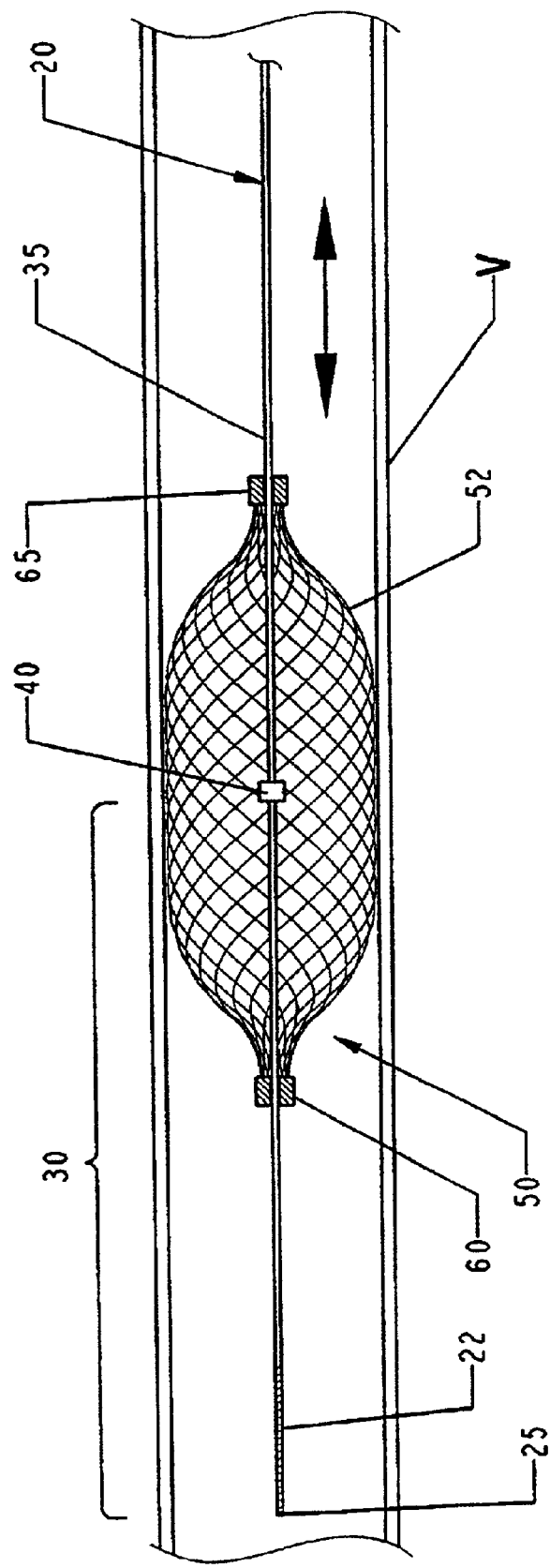
FIG. 3 is a schematic side view in partial cross section of the medical device of FIGS. 1 and 2.
Figure 4:
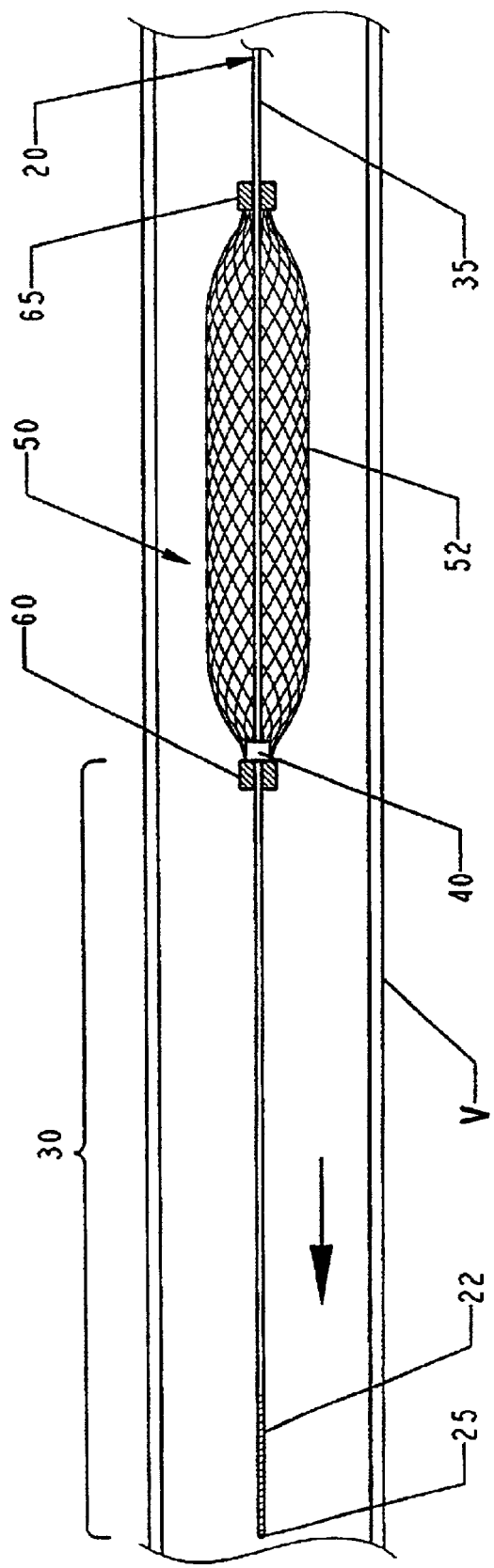
FIG. 4 is a schematic side view in partial cross section of the medical device of FIGS. 1 and 2, but in a partially collapsed configuration induced by urging the mandrel distally.
Figure 5:
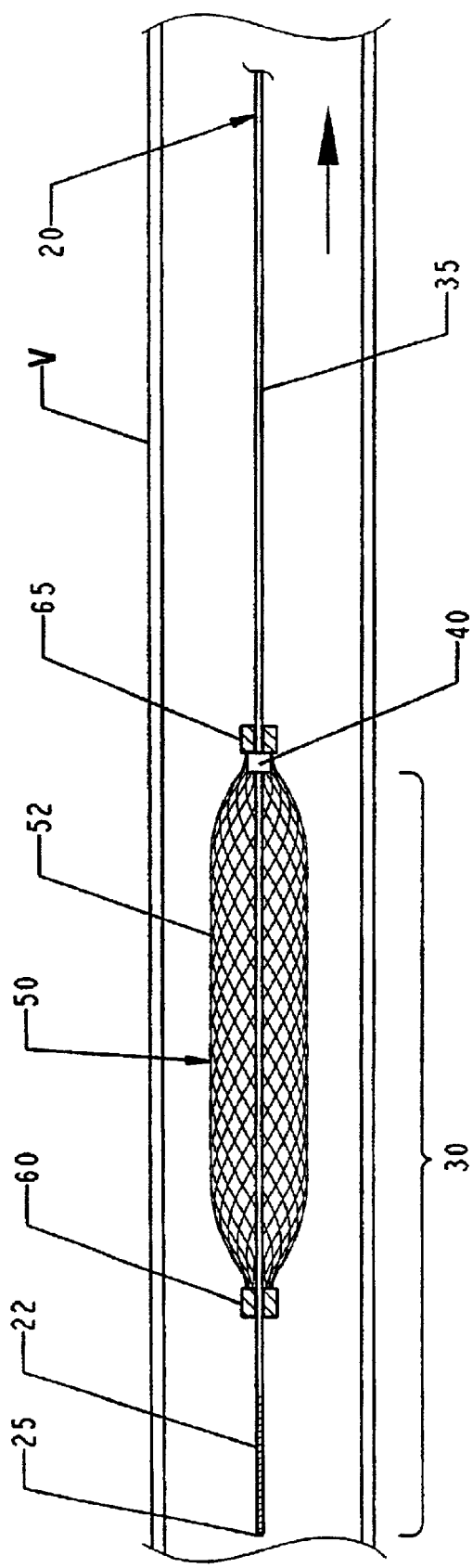
FIG. 5 is a schematic side view in partial cross section of the medical device of FIGS. 1 and 2, but in a partially collapsed configuration induced by proximal withdrawal of the mandrel.

FIGS. 3–5 schematically illustrate the filter system 10 of FIGS. 1 and 2 in partial cross section. In particular, the filter 50 is shown in cross section while the mandrel 20 and its components are shown in side view. This is intended to better illustrate the interaction of the stop 40 of the mandrel and the sliders 60, 65 of the filter 50.

In FIG. 3, the filter 50 is shown in its radially expanded configuration, which it will tend to assume in the absence of any countervailing biasing force. The stop 40 of the mandrel is positioned within the body 52 of the filter and is not exerting any biasing force on either of the sliders 60, 65.

In this configuration, the mandrel 20 can be moved proximally and distally with respect to the filter 50 without substantially affecting the shape or position of the filter. The limits of this range of free movement of the mandrel with respect to the filter are generally defined by the relationship between the stop 40 and the sliders 60, 65. In particular, the mandrel can be moved from a distal position wherein the stop 40 abuts but does not exert any force on the distal slider 60 and a proximal position wherein the stop 40 abuts, but does not exert any significant force on, the proximal slider 65. This allows the filter 50 (or any other functional element which is carried by the mandrel) to be fairly precisely positioned within a patient's vessel and retain that position even if the guidewire is moved slightly during use. This can be advantageous in circumstances where other devices are exchanged over the guidewire (e.g., during angioplasty and atherectomy procedures).

The inner diameter of the generally annular collars defining the sliders 60, 65 is desirably larger than the outer diameter of the mandrel, as mentioned above. However, the inner diameter of these sliders should be smaller than the outer diameter of the stop 40. In this fashion, the stop serves to limit movement of the sliders. As a consequence, the stop 40 serves as an effective limit on proximal movement of the distal slider 60 and distal movement of the proximal slider 65. Apart from this relationship with the slider 40 and the fact that both sliders are indirectly linked to one another by the body 52 of the filter, the proximal and distal sliders are slidable along the mandrel essentially independently of one another.

The advantage of this arrangement is illustrated in FIGS. 4 and 5. In FIG. 4, the mandrel 20 is being urged distally (to the left in this view, as illustrated by the arrow) and urges distally against the distal slider 60. This exerts a distal biasing force against the distal end of the body 52 of the filter. In theory, if the filter were used in a frictionless environment, the filter would travel with the mandrel without any appreciable alteration in the shape of the body 52. In most clinical applications, though, this is not the case. Instead, there is typically some force restraining completely free movement of the filter within the channel of the patient's body. As schematically shown in FIG. 3, the body 52 of the filter may resiliently expand into physical contact with the interior surface of the vessel V. This contact with the vessel wall will tend to hold the filter 50 in place as the stop of the mandrel slides proximally and distally between the two sliders 60, 65. When the mandrel is urged distally until it exerts a distal force against the distal slider 60 (as shown in FIG. 4), this force will tend to axially elongate the body 52.

Resilient tubular braids tend to assume a radially reduced profile upon axial elongation. (This property and some of its implications are discussed in International Publication No. WO 96/01591, mentioned previously. As a consequence, when the mandrel 20 is urged distally to push distally against the distal slider 60, this distal force acts against the restorative force of the resilient braid, which would otherwise bias the braid into its expanded configuration (FIG. 3). By overcoming this restorative force with a countervailing distal force, the body 52 will tend to both axially elongate and assume a radially reduced profile. This, in turn, reduces the force with which the body engages the wall of the vessel V and reduces friction between the filter 50 and the vessel. Hence, urging the mandrel distally to move the filter 50 distally will, at the same time, reduce friction between the filter and the vessel wall to further facilitate advancement of the filter along the vessel's lumen. This requires less force to push the filter distally, enabling the mandrel to be smaller and reducing the outer diameter of the collapsed device, making deployment in smaller vessels feasible. In addition, the reduced friction between the filter and the vessel wall limits damage to the intima of the vessel, permitting the filter to be deployed and moved with a minimum of trauma.

FIG. 5 is similar to FIG. 4, but schematically illustrates what happens upon proximal retraction of the mandrel. In this drawing, the stop 40 of the mandrel abuts against and exerts a proximal biasing force on, the proximal slider 65 of the filter 50. As discussed above in connection with FIG. 4, this proximal biasing force will act against the restorative force of the body 52 to axially elongate and radially reduce that body. This permits the device to be withdrawn proximally along the lumen of the vessel either for repositioning at a more proximal location or for withdrawal from the patient's body at the end of the procedure.

As can be seen by comparing FIG. 3 with FIGS. 4 and 5, the proximal and distal sliders 60, 65 are free to move relatively independently of one another, limited primarily by their indirect link to one another through the body 52 of the filter. For example, when the mandrel 20 is urged distally against the distal slider 60 (FIG. 4), the proximal slider will slide proximally along the proximal length 35 of the mandrel. Similarly, when the mandrel is withdrawn proximally to urge proximally against the proximal slider 65, the distal slider will be free to drift distally along the distal length 30 of the mandrel. Ideally, there should be a sufficient distance between the distal shoulder of the stop 40 and the proximal end of the helical coil 22 at the distal end of the mandrel.

Another salient aspect of the device highlighted in FIGS. 3–5 is that the spacing between the sliders 60 and 65 changes in response to the mandrel acting against one of the sliders. Looking first at FIG. 3, the proximal and distal sliders are spaced a first distance from one another, with the body 52 engaging the wall of the vessel. When the stop 40 of the mandrel urges against one of the sliders, though, the body 52 will tend to axially elongate and the distance between the two sliders will increase.

It should be understood that the change in shape between the radially expanded configuration shown in FIG. 3 and the radially reduced configurations in FIGS. 4 and 5 has been exaggerated to highlight this change. For example, in FIGS. 4 and 5, the body 52 of the filter is shown as being spaced completely away from the wall of the vessel. In most clinical circumstances, though, the body of the filter will still tend to at least lightly engage the intima of the vessel and the change in shape of the body likely will be less dramatic.

Figure 9:
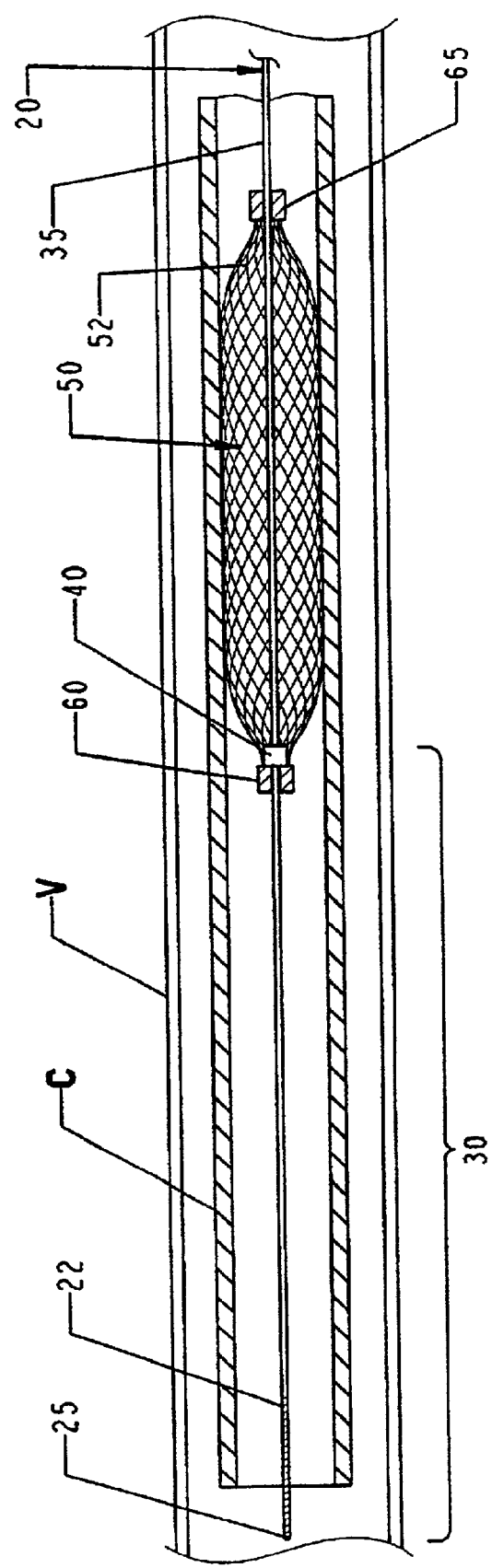
FIG. 9 is a schematic side view in partial cross section of the medical device of FIG. 1, but in a partially collapsed configuration induced by urging the mandrel distally within a catheter.
Figure 10:
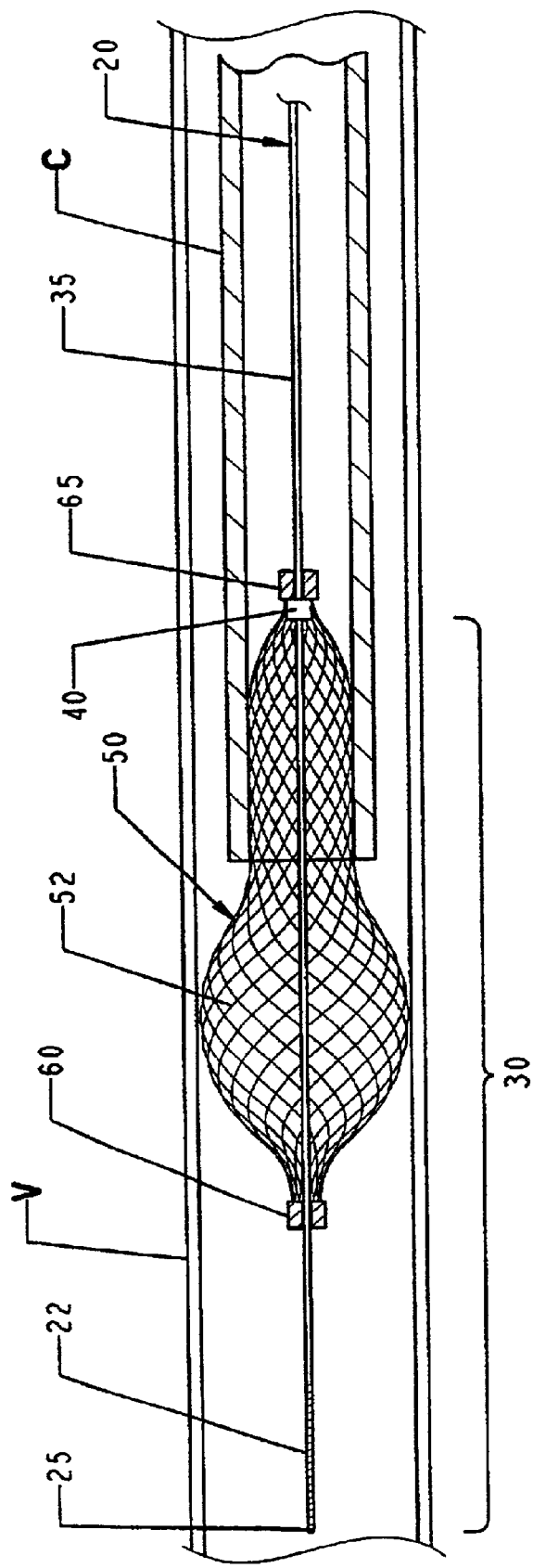
FIG. 10 is a schematic side view in partial cross section of the medical device of FIG. 1, but illustrating how the medical device may be withdrawn using a retrieval catheter.

FIGS. 9 and 10 schematically illustrate certain advantages of the present invention when deploying and retrieving the device in a body channel using a catheter. FIG. 9 schematically shows the device of FIGS. 1–5 being deployed through a catheter C. In particular, a length of the mandrel 20 and the entirety of the filter 50 is received within the lumen of the catheter C. The mandrel 20 is being urged distally to exit the distal end of the catheter C. The stop 40 is exerting a distal biasing force against the distal slider 60 within the relatively close confines of the catheter C. The body 52 of the filter 50 will exert an outward force against the interior surface of the catheter C, increasing friction between the filter and the catheter C. The distal biasing force of the stop 40 acting against the slider 60 will tend to axially elongate and radially reduce the body 52 of the filter, thereby reducing friction between the filter and the catheter C. This can significantly ease the deployment of the device through the catheter C. FIG. 10 schematically illustrates retrieval of the device of FIGS. 1–5 and 9 which has already been deployed in a patient's vessel. In particular, the filter 50 is being withdrawn proximally into the lumen of the catheter C. This can be initiated by positioning the distal end of the catheter C just proximal of the proximal slider 65 and then moving the catheter C with respect to the stop 40. This can be accomplished either by urging the catheter C distally or withdrawing the mandrel 20 proximally, as the operator sees fit at the time.

The catheter C will frictionally engage and will tend to radially compress the body 52 of the filter. As a consequence, the slider 65 will be brought in contact with the stop 40. Further movement of the catheter C with respect to the mandrel will urge more of the length of the body 52 into the lumen of the catheter C. At the same time, the distal slider 60 may slide distally along the distal length 30 of the mandrel, permitting the body 52 to axially elongate in response to the radial compression induced by the catheter C.

These two figures highlight some of the advantages of this embodiment of the invention. In particular, the body 52 of the filter will axially elongate and radially reduce in response to movement of the mandrel 20 with respect to the catheter C. In deploying the device (FIG. 9), the stop 40 urges distally against the distal slider 60, effectively pushing the filter 50 distally along the catheter C. In retrieving the device (either for repositioning or for removal from the patient's body), the stop 40 can be seen as pushing proximally on the proximal slider 65. Again, this biasing force will tend to axially elongate and radially reduce the body 52 of the filter. This axial elongation and radial reduction of the body 52 in FIGS. 9 and 10 reduces friction with the lumen. In addition, the radial reduction of the body during retrieval into the catheter C (FIG. 10) facilitates collapse of the filter into the lumen of the catheter C, making it easier to introduce the filter into the catheter. This same ability can also be used advantageously in initially deploying the filter, as explained below.

As noted above, FIGS. 7 and 8 illustrate an alternative embodiment of the invention. There are numerous similarities between the device shown in FIGS. 1–6 and that shown in FIGS. 7 and 8. In order to simplify discussion, elements in FIGS. 7 and 8 performing a function analogous to an element in FIGS. 1–6 bear the same reference numeral, but incremented by 100. Hence, FIGS. 1–6 refer to a filter system 10 having a mandrel 20; FIGS. 7 and 8 show a filter system 110 having a mandrel 120.

The primary difference between the filter 150 of FIGS. 7 and 8 and the filter 50 of FIGS. 1–6 is the shape of the filter in its fully radially expanded configuration. The filter 50 has a generally tubular body with spaced-apart tapered ends. In contrast, the filter 150 of FIGS. 7 and 8 has a generally umbrella-shaped body 152, with a proximal length of the fabric defining the body being inverted and received within the interior of the distal portion of the fabric. As a consequence, the distal slider 160 and proximal slider 165 are positioned much more closely to one another in the fully deployed filter 150, shown in FIG. 7, than are the spacers 60, 65 in the fully deployed filter 50, shown in FIGS. 1–3.

FIG. 8 illustrates the filter 150 in an axially elongated, radially reduced state induced by withdrawing the mandrel 120 proximally. When the mandrel 120 is withdrawn proximally within the patient's vessel, the stop 140 will abut and urge proximally against the proximal slider 165. In the embodiment of FIGS. 1–5, 9 and 10, this tends to axially elongate the body 52 of that filter 50 without any substantial change in the shape of the filter. The filter 150 of FIGS. 7 and 8 is more complex in its fully deployed, expanded state (shown in FIG. 7). Rather than simply axially elongating and radially reducing the shape shown in FIG. 7, the proximal length of the fabric which is received within the interior of the distal portion of the fabric will tend to evert. The distal portion of the fabric (i.e., the outer portion of the fabric shown in FIG. 7) will tend to remain in place in frictional engagement with the wall of the vessel during this process. As a consequence, the shape of the interior surface of the umbrella will change first without any significant change in the external shape.

As the mandrel continues to be withdrawn and the proximal and distal sliders 165, 160 are moved farther apart, the body 152 will take on a shape which looks more like the shape of the filter 50 of the previous embodiment. Continuing to urge proximally against the proximal slider 165 will further elongate the body until it reaches a shape such as that schematically illustrated in FIG. 8. This makes withdrawal of the trap easier, but care should be taken to ensure that any particular material retained within the interior of the umbrella-like body 152 is not inadvertently dumped back into the patient's bloodstream. This can be done, for example, by breaking down trapped thrombus using clot-busting drugs or by aspirating the particulate material through a catheter before proximally withdrawing the mandrel 120.

In one particularly useful process for withdrawing the deployed filter 150 from a patient's bloodstream, a catheter C is urged distally along the proximal length 135 of the mandrel until the distal tip of the catheter (not shown in FIGS. 7 and 8) is positioned in the interior of the umbrella-like filter body 152. If necessary, any particulate material within that interior can be aspirated through the catheter C and out of the patient's body. Thereafter, the mandrel can be withdrawn proximally, drawing the proximal slider 165 into the interior of the catheter C. As discussed above in connection with FIG. 10, this will help collapse the body 152 of the filter into the lumen of the catheter C. If so desired, the catheter C can be held in the same position while the rest of the filter 150 is drawn inside. Alternatively, the catheter C and the mandrel can be withdrawn together as a unit a short distance so that the distal tip of the catheter C is positioned slightly proximal of the proximal edge of the deployed filter shown in FIG. 7. This will further facilitate drawing the body 152 down into the lumen of the catheter C. Once at least the majority of the filter 150 is received within the lumen of the catheter C, the catheter, the filter and the mandrel 120 can be withdrawn together as a unit from the patient's body.

FIG. 11 shows a medical device which is similar to the embodiment shown in FIGS. 1–5, 9 and 10. However, the shape of the body 52' of the plug 50' has a significantly different shape from the body 52 of the filter 50 discussed above. Whereas the majority of the length of the filter 50 would assume a relatively constant diameter if left unconstrained, the body 52' of the plug 50' has a more complex shape. While this device can also be used to filter fluid which is passing through a vessel, its design is particularly well-suited to occlude a vessel either temporarily or permanently.

A method for making and using a vascular occlusion device having a shape similar to that of the body 52' of FIG. 11 is disclosed in International Publication No. WO 96/01591, the teachings of which were incorporated above. Briefly, though, this body 52' includes a pair of spaced-apart enlarged diameter sections separated by a central section having a reduced diameter. If so desired, the surface of this device may be coated with a thrombogenic agent or nylon fibers or the like can be attached to the body 52'. Conversely, if the plug 50' or the filter 50 are to be used solely for purposes of filtering fluids passing therethrough and it is preferred that any blood passing through the functional element not clot thereon, the body can be coated with an anti-thrombogenic agent.

One of the difficulties encountered in using the vascular occlusion device disclosed in International Publication No. WO 96/01591 is the friction between the body of the vascular occlusion device and the catheter through which it is deployed. The stop 40 urging against the distal slider 60 of FIG. 11 will tend to axially elongate and radially reduce the body 52' of the plug 50' as it is urged along the catheter C. This will reduce friction between the plug 50' and the catheter C, making it significantly easier to deploy the device at the desired treatment site. The present design also facilitates repositioning of the plug 50' if its initial deployment is not precisely at the desired location. In particular, withdrawing the mandrel 20 proximally will exert a proximal biasing force on the proximal slider 65, facilitating withdrawal of the device into the deployment catheter, much as discussed above in connection with FIG. 10. Once the plug is sufficiently retracted into the catheter, the catheter can be repositioned and the plug can be deployed distally out of the catheter again at the new location.

The plug 50' of FIG. 11 can be used as a temporary occlusion device and withdrawn at the end of a procedure or treatment course. In other circumstances, though, it may be preferred to more permanently occlude the channel in which the plug 50' is deployed. While the stop 40 abutting against the sliders 60, 65 facilitates deployment and repositioning, the attachment of the stop 40 to the mandrel 20 could effectively prevent one from removing the mandrel from the plug.

The mandrel 20 can be withdrawn either partially or entirely from the plug in a variety of different manners. For example, the proximal portion 35 of the mandrel can be releasably attached to the stop 40, e.g., by means of a threaded engagement therebetween. Without somehow locking the distal section 30 against rotation (e.g., by a splined connection between the distal section 30 and the distal slider 60), though, it can be difficult to disconnect these parts from one another.

Figure 12:
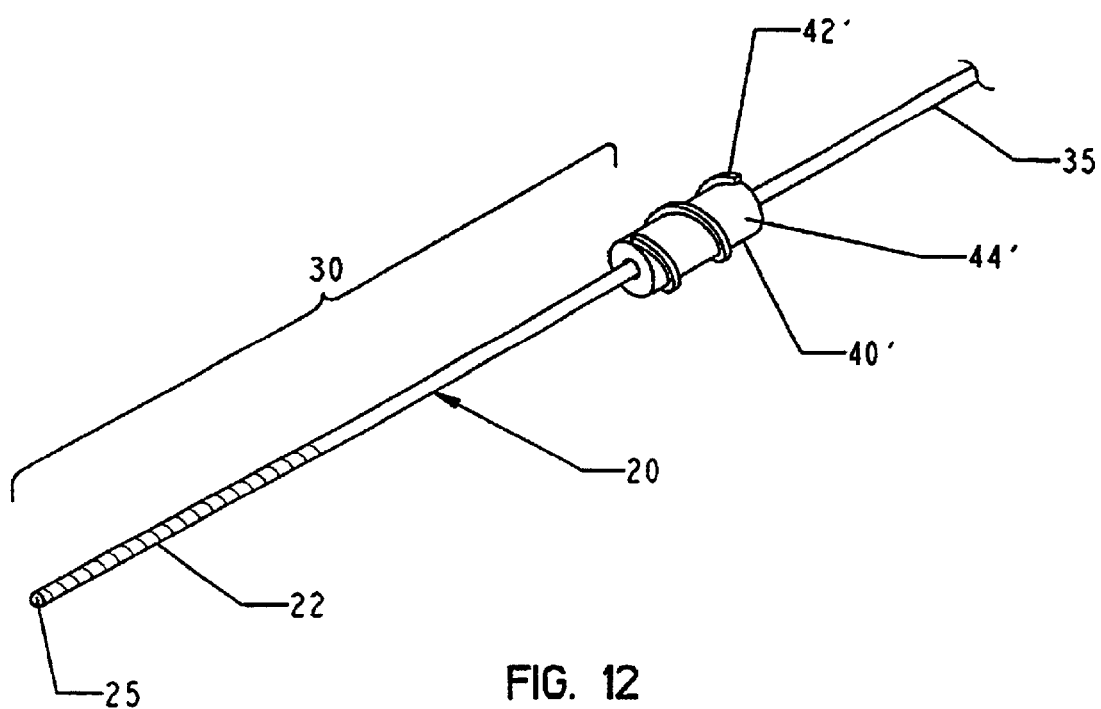
FIG. 12 is a schematic perspective view of a stop of the invention which may be used to facilitate withdrawal of the mandrel for permanent deployment of a medical device.

FIG. 12 illustrates one preferred embodiment of a stop 40' which may be used to withdraw the mandrel 20 while leaving the filter 50 or plug 50' in place in the patient's body. In the prior embodiments, the stop 40 and the proximal slider 65 were both essentially annular in shape, with the relatively constant outer diameter of the stop being greater than the relatively constant inner diameter of the slider. As a consequence, one cannot readily withdraw the stop 40 from within the enclosure of the body 52 of the filter 50.

The stop 40' of FIG. 12, however, can be withdrawn from the interior of a filter 50, plug 50' or other device having a suitably adapted proximal slider. The stop 40' includes an external thread 42' which extends spirally outwardly from the main body 44' of the stop. The proximal slider (not shown in this view) has a threaded internal surface which is sized and shaped to mate with the outer thread 42' on the stop 40'. Aside from the spiral slot or keyway shaped to receive the thread 42' of the stop, the inner diameter of the proximal slider should be slightly greater than the outer diameter of the body 44' of the stop but less than the maximum diameter of the stop including the thread 42'. During normal operation, this will ensure that the stop 40' will abut against the proximal slider so the device will operate as described above.

If an operator decides to leave the filter 50 or plug 50' in place, though, the mandrel can be withdrawn from the filter or plug by pulling the mandrel proximally until the stop 40 lightly abuts the proximal slider. Rotating the mandrel about its axis will permit the thread 42' to travel along the slot in the proximal slider. In this manner, the stop can be withdrawn through the proximal slider and the mandrel can be completely removed from the patient's body, leaving the medical device in place within the vessel.

The present invention also contemplates a method of employing a medical device in a channel in a patient's body. For the sake of convenience, the following discussion will make reference to FIG. 1–5 and the reference numbers used therein. It should be understood, though, that this method can be used with any of a wide variety of medical devices having different functional elements (including the plug 50' and the drainage catheter 250 illustrated in other drawings) and need not be limited to a filter system 10 having a filter 50 as its functional element.

In accordance with this method, the medical device is introduced into a vessel in a patient's body. In the medical device 10 shown in FIGS. 1–5, this would comprise inserting the distal end 25 of the mandrel 20 into the lumen of the patient's vessel V. This may be done either directly or, more commonly, by using an introducer sheath. Such introducer sheaths are commonly used in introducing medical devices for minimally invasive procedures. Once the mandrel is introduced into the vessel, the mandrel can be urged distally to introduce the functional element, i.e., filter 50 in FIGS. 1–5, and to the vessel, as well. Using the filter system 10 of FIGS. 1–5, this can be accomplished simply by urging the mandrel distally and allowing both the action of the stop 40 against the distal slider 60 and the contact with the wall of the introducer sheath to collapse the filter body 50 into a radially reduced configuration. The same tendency of the filter body 52 to axially elongate and radially reduce discussed above in connection with FIG. 4 will also reduce friction between the filter body 52 and the interior surface of the introducer sheath as the filter is advanced therealong.

The filter 50 may be urged distally along the lumen of the vessel V to a predetermined treatment site. The treatment site may, for example, simply be a convenient location in a patient's vasculature positioned distally of an obstruction which will be treated with an angioplasty balloon or an atherectomy device. As explained above, the filter 50 can be advanced along the vessel by urging the mandrel distally such that the stop 40 engages the distal slider 60. This exerts a distal biasing force on the distal slider which, in turn, acts against a restorative force of the body 52 of the filter. As a result, the body 52 will tend to axially elongate and take on a radially reduced profile. This reduces friction between the filter 50 and the wall of the vessel, facilitating advancement therealong.

Once the filter has reached the desired treatment site, the axial force against the mandrel can simply be released. This will permit the body 52 to expand radially and axially contract, drawing the two sliders 60, 65 toward one another along the mandrel. If it is determined that the filter is not precisely positioned in the desired treatment site, it can be readily repositioned by pushing the mandrel distally or withdrawing it proximally and again allowing the filter to self-expand radially and self-contract axially once the mandrel stops acting against the sliders. When it comes time to remove the filter 50 from the patient's vessel or move it proximally to a new treatment site, the operator can simply pull proximally on the mandrel to radially contract the device and facilitate proximal movement within the vessel, as shown in FIG. 5.

In some circumstances, one may wish to limit the trauma to the intima of the vessel walls which may otherwise occur as the filter 50 is dragged along the vessel to the desired treatment site. This can be accomplished using a catheter to position the device adjacent the desired treatment site and/or to withdraw the device from the vessel after it has been deployed.

In accordance with one such method, a catheter may be positioned adjacent a treatment site in a patient's body. This can be done in any desired fashion. For example, the mandrel 20 and the catheter can be advanced simultaneously through the patient's vessel. In a particularly preferred embodiment, though, the catheter will be positioned at the desired treatment site before the mandrel 20 is inserted into the catheter. This permits the operator to steer the catheter into place without hindrance from the mandrel or to track the catheter over a guidewire if the desired treatment site is positioned in a narrower or more tortuous vessel, after which the guidewire can be removed.

Once the distal tip of the catheter is positioned adjacent the treatment site, the distal tip 25 of the mandrel can be inserted into the proximal end (not shown) of the catheter outside the patient's body. Once the distal slider 60 of the filter 50 enters the proximal end of the catheter, the catheter will frictionally engage the body 52 of the filter. Further distal urging of the mandrel will cause the stop 40 to exert a distal biasing force on the distal slider 60. Much like the process shown in FIG. 10, this distal biasing force will tend to axially elongate and radially reduce the body 52, further facilitating entry of the body into the lumen of the catheter.

Once the filter 50 is received within the catheter, it may continue to be urged distally along the length of the catheter. As explained above in connection with FIG. 9, the distal urging of the stop 40 against the distal slider 60 will axially elongate and radially reduce the body, reducing friction between the body and the catheter during such advancement. If the distal tip of the catheter is positioned just proximally of the desired treatment site, the mandrel can be urged distally until the device exits the distal end of the catheter. Preferably, the body will then tend to radially self-expand until it reaches a radially-expanded shape wherein it may engage the walls of the vessel (B in FIG. 9). Alternatively, the distal tip of the catheter may be positioned distally of the desired treatment site. In such a circumstance, advancement of the mandrel can be stopped when the operator determines by means of the radiopaque sliders 60, 65 that the filter is in the desired treatment site. Thereafter, the catheter can be withdrawn proximally while holding the mandrel 20 in place. As the distal tip of the catheter is withdrawn proximally from the body 52 of the device, the body will tend to radially self-expand with the distal slider 60 remaining in substantially the same place due to its abutment against the stop 40.

In many circumstances, one may wish to deploy the filter 50 in a temporary fashion so that it may be readily withdrawn in the manner discussed below. In other circumstances, though, it may be desirable to leave the device in place in the patient's body for an extended period of time or even permanently. This is the most likely scenario for a plug 50' deployed in a patient's vascular system as a vascular occlusion device, for example.

It is preferred that the mandrel be withdrawn from the patient's body either in part or in its entirety. By establishing a selectively disengageable connection between one length of the mandrel and another length, the distal most of those lengths can be detached from one another, leaving the filter 50 and the distal-most length in the patient's body while withdrawing the proximal-most length. These lengths can be connected in any fashion known in the art, such as by means of a threaded engagement or by means of a solder which can be melted or softened by application of electrical resistance heating of the mandrel.

More preferably, though, the entire mandrel 20 is withdrawn from the patient's body. This can be done by withdrawing the stop 40 through the proximal slider 65 of the filter. One suitable stop 40' is shown in FIG. 12. This stop 40', used in conjunction with a specially adapted proximal slider (not shown, but described above) can be used to withdraw the stop through the proximal slider for removal of the mandrel. As explained previously, this can be accomplished by bringing the stop 40' into abutting engagement with the proximal slider then rotating the mandrel 20 about its axis. This will cause the thread 42' extending radially outwardly from the body 44' of the stop to pass along a mating slot in the proximal slider. After the mandrel has been rotated sufficiently to completely withdraw the stop through the proximal slider, the mandrel can easily be withdrawn from the body by withdrawing the distal portion 30 of the mandrel proximally through the center of the filter body 52 and out of the patient's body entirely.

If the device is not to be permanently left in its original position, one can withdraw the filter 50 from the body by withdrawing it into the lumen of the catheter C. This can be done either to withdraw the filter 50 from the patient's body at the end of a procedure or simply for purposes of repositioning the filter at a new location. As discussed above in more detail in connection with FIG. 10, the filter 50 can be withdrawn into the lumen of the catheter C either by holding the mandrel stationary and advancing the catheter distally over the filter 50 or by holding the catheter in a fixed position and withdrawing the mandrel 20 proximally. Either way, the proximal urging of the stop 40 against the proximal slider 65 tends to axially elongate and radially reduce the body 52, both facilitating entry of the body 52 into the lumen of the catheter and reducing friction between the catheter and the length of the body 52 which is already received therein. Once the filter 50 is received within the catheter, the catheter may be held in place and the mandrel 20 and filter 50 can be completely removed from the catheter. Alternatively, the catheter, mandrel and filter 50 can all be removed simultaneously as a unit from the patient's body.

While a preferred embodiment of the present invention has been described, it should be understood that various changes, adaptations and modifications may be made therein without departing from the spirit of the invention and the scope of the appended claims.

What is claimed is:

1. A collapsible medical device comprising:
   a) a mandrel having a distal end and a stop spaced proximally of the distal end, a proximal length of the mandrel extending proximally of the stop and a distal length of the mandrel extending distally of the stop, wherein the proximal length of the mandrel has a proximal diameter and the distal length of the mandrel has a distal diameter and wherein the proximal and distal diameters are substantially equal; and
   b) a functional element comprising a radially expandable body having a proximal slider and a distal slider, the proximal slider being slidably carried along the proximal length of the mandrel and the distal slider being slidably carried along the distal length of the mandrel, the proximal and distal sliders being slidable along the mandrel independently of one another such that the distance between the proximal slider and distal slider can be varied to effect different configurations of the functional element.

2. The medical device of claim 1 wherein the functional element has an expanded configuration and is capable of being collapsed for passage along a lumen, the functional element being adapted to resiliently return toward the expanded configuration in the absence of any biasing force.

3. The medical device of claim 1 wherein the body of the functional element assumes a radially reduced configuration when the distance between the proximal slider and the distal slider is increased.

4. The medical device of claim 3 wherein the stop abuts the proximal slider and exerts a proximal biasing force thereon, such proximal biasing force acting against a restorative force of the body to axially elongate and radially reduce the body.

5. The medical device of claim 3 wherein the stop abuts the distal slider and exerts a distal biasing force thereon, such distal biasing force acting against a restorative force of the body to axially elongate and radially reduce the body.

6. The medical device of claim 5 wherein a wall of the control sheath exerts a biasing force against a radially restorative force of the body, such biasing force maintaining a space between the proximal and distal sliders.

7. The medical device of claim 1 further comprising a control sheath, the body being collapsed within the sheath with the proximal and distal sliders spaced from one another.

8. The medical device of claim 1 wherein the proximal slider comprises a proximal annular ring defining an opening having an inner diameter and the distal slider comprises a distal annular ring defining an opening having an inner diameter and wherein the inner diameter of the openings in the proximal and distal annular rings are substantially equal.

9. A collapsible medical device comprising:
   a) a mandrel having a distal end and a stop spaced proximally of the distal end, a proximal length of the mandrel extending proximally of the stop and a distal length of the mandrel extending distally of the stop; and
   b) a functional element comprising a radially expandable body having a radially expanded configuration and adapted to resiliently assume the radially expanded configuration in the absence of a countervailing biasing force, the body being attached to the mandrel by a proximal slider and a distal slider, the proximal slider being slidably carried along the proximal length of the mandrel and the distal slider being slidably carried along the distal length of the mandrel, the proximal and distal sliders being slidable along the mandrel independently of one another such that the distance between the proximal slider and distal slider can be varied to effect different configurations of the body, wherein the proximal slider comprises a proximal annular ring defining an opening having an inner diameter and the distal slider comprises a distal annular ring defining an opening having an inner diameter and wherein the inner diameter of the openings in the proximal and distal annular rings are substantially equal.

10. The medical device of claim 9 wherein the proximal length of the mandrel has a proximal diameter and the distal length of the mandrel has a distal diameter and wherein the proximal and distal diameters are substantially equal.

11. A collapsible medical device comprising:
   a) a mandrel having a distal end and a stop spaced proximally of the distal end, a proximal length of the mandrel extending proximally of the stop and a distal length of the mandrel extending distally of the stop, wherein the proximal length of the mandrel has a proximal diameter and the distal length of the mandrel has a distal diameter and wherein the proximal and distal diameters are substantially equal; and
   b) a functional element formed of a resilient tubular braid which has a preferred radially expanded configuration but will assume a radially reduced profile upon axial elongation, proximal and distal sliders being attached to the tubular braid with a length of the braid extending therebetween, the proximal slider being slidably carried along the proximal length of the mandrel and the distal slider being slidably carried along the distal length of the mandrel, the proximal and distal sliders being slidable along the mandrel independently of one another.

12. The medical device of claim 11 wherein the stop has an external diameter larger than an internal diameter of either the proximal slider or the distal slider.

13. The medical device of claim 11 wherein the stop is sized to urge distally against the distal slider upon distal urging of the mandrel, such distal urging thereby axially elongating the functional element to facilitate its advancement along a lumen.

14. The medical device of claim 11 wherein the proximal slider comprises a proximal annular ring defining an opening having an inner diameter and the distal slider comprises a distal annular ring defining an opening having an inner diameter and wherein the inner diameter of the openings in the proximal and distal annular rings are substantially equal.

15. A filter system for temporary deployment in a channel of a patient's body, comprising:
   a) a mandrel having a distal end and an enlarged diameter stop spaced proximally of the distal end; and
   b) a filter formed of a resilient tubular braid and including proximal and distal sliders, the proximal slider being slidably carried along the mandrel proximally of the stop and the distal slider being carried along the mandrel between the stop and the distal end of the mandrel, the filter having a collapsed configuration wherein the sliders are spaced from one another a first distance along the mandrel and the filter has a first diameter, and an expanded configuration wherein the sliders are spaced a second, shorter distance along the mandrel and the filter has a second diameter, the first diameter being less than the second diameter, wherein the proximal slider comprises a proximal annular ring defining an opening having an inner diameter and the distal slider comprises a distal annular ring defining an opening having an inner diameter and wherein the inner diameter of the openings in the proximal and distal annular rings are substantially equal.

16. The filter of claim 15 wherein each of the proximal and distal sliders comprises an annular collar having an inner diameter larger than an outer diameter of the mandrel but smaller than an outer diameter of the stop, the stop thereby serving to limit movement of the sliders.

17. The filter of claim 15 wherein the proximal and distal sliders are slidable along the mandrel independently of one another.

18. The filter of claim 15 wherein the stop abuts the proximal slider and exerts a proximal biasing force thereon, such proximal biasing force acting against a restorative force of the filter to axially elongate and radially reduce the filter.

19. The filter of claim 15 wherein the stop abuts the distal slider and exerts a distal biasing force thereon, such distal biasing force acting against a restorative force of the filter to axially elongate and radially reduce the filter.

20. The filter of claim 15 wherein the proximal length of the mandrel has a proximal diameter and the distal length of the mandrel has a distal diameter and wherein the proximal and distal diameters are substantially equal.

21. A method of employing a medical device in a lumen of a vessel, comprising:
   a) providing a collapsible medical device comprising a mandrel having a distal end and a stop spaced proximally of the distal end, wherein the proximal length of the mandrel has a proximal diameter and the distal length of the mandrel has a distal diameter and wherein the proximal and distal diameters are substantially equal; and a functional element formed of a resilient tubular braid and including proximal and distal sliders, the proximal slider being slidably carried along the mandrel proximally of the stop and the distal slider being carried along the mandrel between the stop and the distal end of the mandrel;
   b) inserting the distal end of the mandrel in the lumen and urging the functional element distally along the lumen to a treatment site by urging the mandrel distally such that the stop engages the distal slider and exerts a distal biasing force thereon, such distal biasing force acting against a restorative force of the functional element to axially elongate the functional element and reduce friction between the functional element and a wall of the vessel.

22. The method of claim 21 wherein the proximal slider and distal slider are permitted to slide along the mandrel independently of one another.

23. The method of claim 21 further comprising allowing the functional element to resiliently self-expand radially and self-contract axially by ceasing the distal urging of the mandrel when the functional element reaches the treatment site.

24. The method of claim 21 further comprising moving the functional element proximally along the lumen by withdrawing the mandrel proximally such that the stop engages the proximal slider and exerts a proximal biasing force thereon, such proximal biasing force acting against a restorative force of the filter to axially elongate the filter and reduce friction between the functional element and the wall of the vessel.

25. The method of claim 21 wherein the proximal slider comprises a proximal annular ring defining an opening having an inner diameter and the distal slider comprises a distal annular ring defining an opening having an inner diameter and wherein the inner diameter of the openings in the proximal and distal annular rings are substantially equal.

\* \* \* \* \*